United States Patent
Chen et al.

(10) Patent No.: US 10,006,067 B2
(45) Date of Patent: Jun. 26, 2018

(54) METHOD FOR PRODUCING DHA THROUGH SOLID CULTURE AND LIQUID FERMENTATION OF SCHIZOCHYTRIUM

(71) Applicants: Xiamen Kingdomway Group Company, Xiamen (CN); Inner Mongolia Kingdomway Pharmaceutical Limited, Huhhot (CN)

(72) Inventors: Jinqing Chen, Xiamen (CN); Fangfang Chen, Xiamen (CN); Junhuang Chen, Xiamen (CN); Chao Lin, Xiamen (CN); Meiqiong Wu, Xiamen (CN)

(73) Assignees: Xiamen Kingdomway Group Company, Xiamen, Fujian (CN); Inner Mongolia Kingdomway Pharmaceutical Limited, Huhhot, Inner Mongolia (CN)

( * ) Notice: Subject to any disclaimer, the term of this patent is extended or adjusted under 35 U.S.C. 154(b) by 104 days.

(21) Appl. No.: 14/654,897

(22) PCT Filed: Dec. 30, 2013

(86) PCT No.: PCT/CN2013/090839
§ 371 (c)(1),
(2) Date: Jun. 23, 2015

(87) PCT Pub. No.: WO2014/101857
PCT Pub. Date: Jul. 3, 2014

(65) Prior Publication Data
US 2015/0361461 A1    Dec. 17, 2015

(30) Foreign Application Priority Data
Dec. 31, 2012    (CN) .......................... 2012 1 0593090

(51) Int. Cl.
C12P 7/64    (2006.01)
C12R 1/89    (2006.01)
(52) U.S. Cl.
CPC .............. *C12P 7/6427* (2013.01); *C12R 1/89* (2013.01)
(58) Field of Classification Search
CPC ................................. C12P 7/6427; C12R 1/89
See application file for complete search history.

(56) References Cited

U.S. PATENT DOCUMENTS

2011/0306102 A1    12/2011    Ratnam et al.

FOREIGN PATENT DOCUMENTS

| CN | 101638361 A | * | 2/2010 |
| CN | 101812484 A | * | 8/2010 |
| CN | 101886044 A |   | 11/2010 |
| CN | 102333880 A |   | 1/2012 |
| CN | 103146584 A |   | 6/2013 |

OTHER PUBLICATIONS

Chaung et al. (2012) AMB Express 2:42 doi:10.1186/2191-0855-2-42 (Year: 2012).*
Chen et al., Journal of Xiamen University (Natural Science), vol. 48(1):84-8 (2009) w/English Abstract.
Chen et al., Science-Engineering (A), China Master's Theses Full-Text Database, No. 2, ISSN 1674-0246, pp. 1-78 (2007) w/English Abstract.
PCT/CN2013/090839 International Search Report by Xiangyu Wang dated Apr. 3, 2014.
Ren et al., Chinese Journal of Bioprocess Engineering, vol. 10(1):42-5 (2012) w/English Abstract.

* cited by examiner

*Primary Examiner* — Lisa J Hobbs
(74) *Attorney, Agent, or Firm* — RatnerPrestia

(57) ABSTRACT

The invention relates to a method for fermentation production of DHA, in particular a method for producing DHA through solid culture and liquid fermentation of *Schizochytrium*. The method comprises steps of activation of a strain, preparation of a suspension of the strain, preparation of a primary seed, preparation of a secondary solid seed, enlarging cultivation of the secondary solid seed in a fermentor, collection of cells after fermentation, and extraction of DHA oil. With the fermentation method, the seed preparation method is improved, the seed enlarging technology is simplified, the period of seed culture and fermentation is shortened, and therefore the investment is reduced and the cost is saved; in addition, the solid culture medium is of eutrophy and rich in a plurality of growth factors, and is more beneficial to the growth of the seed; cells are strong in viability and good in synchronism in solid culture medium.

9 Claims, No Drawings

METHOD FOR PRODUCING DHA THROUGH SOLID CULTURE AND LIQUID FERMENTATION OF SCHIZOCHYTRIUM

CROSS-REFERENCE TO RELATED APPLICATIONS

This application is a U.S. National Phase Application of PCT International Application PCT/CN2013/090839, filed Dec. 30, 2013, which claims priority to Chinese Application No. 201210593090.0, filed Dec. 31, 2012, the contents of each of which are incorporated herein by reference in their entireties for all purposes.

TECHNICAL FIELD

The invention relates to a method for fermentation production of DHA, in particular a method for producing DHA through solid culture and liquid fermentation of *Schizochytrium*.

BACKGROUND OF THE INVENTION

Docosahexaenoic acid (22: 6 Δ4, 7, 10, 13, 16, 19, referred to as DHA), commonly called "brain gold", belongs to ω-3 polyunsaturated fatty acid and has the physiological functions of brain fitness, prevention of senile dementia, improvement of eyesight, prevention and treatment of myopia, prevention of hypertension, arteriosclerosis and arthritis, treatment of cancers and etc. Therefore, DHA has broad market prospects as a new generation of functional health factor. With increasing market demands, the requirement for DHA quality becomes higher and higher, the direction of research on producing DHA has been gradually developed towards biosynthesis, and DHA from traditional fish oil has been gradually replaced by algal oil DHA. The algal oil DHA refers to oil containing DHA and other long-chain polyunsaturated fatty acids obtained by microbial fermentation, wherein DHA-producing fungi mainly comprise *Schizochytrium, Thraustochytrium, Crypthecodinium* and etc.

*Schizochytrium*, also named as *Schizochytrium limacinum*, is unicellular, spherical and one kind of algae-like marine fungi, which belongs to Thraustochytriaceae, Saprolegniales, Oomycetes, Eumycota. A large amount of active substances which are useful to human bodies are accumulated within the cell, such as oil, pigments (carotenoids, lutein and astaxanthin), squalene and etc., wherein the content of DHA in total fatty acids is up to 35%-45%, and more than 90% of oil in the cell exists in neutral oil form, i.e. triglyceride, which is easily absorbed by human body. Thereby *Schizochytrium* is an ideal strain for producing DHA.

Chinese patent CN101575584 discloses *Schizochytrium* sp. and method for producing DHA oil by using same. The method optimizes a strain fermentation medium from the perspectives of osmotic pressure and element supply, combines a fed-batch strategy to achieve high-density fermentation of *Schizochytrium*, and adopts a traditional fermentation method, which comprises the steps of inoculating seeds saved in glycerine into a shake flask to activate, preparing a primary seed solution, preparing a secondary seed solution in the shake flask, culturing in a primary seed tank, culturing in a secondary seed tank and fermenting, thus the final dry cell weight reaches 70 g/L, the oil content reaches 31.5 g/L, and the DHA accounts for more than 35% of the total fatty acids content.

Chinese patent CN101519676 discloses a fermentation production process for production of DHA by using a fermentation culture medium containing trace elements, which includes using traditional method to culture *Schizochytrium* strain, namely slant activation culture, then enlarging culture by transferring into a shake flask, and performing primary enlarging culture to obtain a seed solution for fermentation; or culturing with slant activation, than enlarging culture by transferring into a shake flask, and performing primary enlarging culture and secondary enlarging culture to obtain a seed solution for fermentation, and by fermenting in a 10T tank for 95 h, the biomass is 53 g/L, the oil content is 72%, and the content of DHA is 50%.

However, the above mentioned traditional seed culture and fermentation method involves many fermentation stages, the process is very complicated, the culture period is long and the investment cost is high. Thus, it is urgent in the art to improve seed preparation method, simplify seed enlarging process, and reduce the production cost, to benefit the production of DHA.

SUMMARY OF THE INVENTION

The objective of the invention is to provide a method for producing DHA through solid culture and liquid fermentation of *Schizochytrium*, in which the seed enlarging technology is simplified, the period of seed culture and fermentation is shortened, the investment is reduced and the cost is saved; in addition, the solid culture medium is of eutrophy and rich in a plurality of growth factors, and is more beneficial to the growth of seeds, cells are strong in viability and good in synchronism; besides, there are less waste water and waste residue which are generated in the stage of solid culture of seed, and has less environmental pollution.

DETAILED DESCRIPTION OF THE INVENTION

The first aspect of the invention relates to a method for producing DHA through solid culture and liquid fermentation of *Schizochytrium*, which comprises the following steps:

(1) activation of a strain: a *Schizochytrium* strain is inoculated into a culture medium (for example, a slant culture medium), cultured and activated to prepare a suspension of the strain;

(2) preparation of a primary seed: the suspension of the strain obtained in step (1) is inoculated into a solid culture medium and cultured to obtain a primary solid seed; or the suspension of the strain obtained in step (1) is inoculated into a liquid seed culture medium and cultured (for example, by shake-flask culture) to obtain a primary liquid seed;

(3) preparation of a secondary solid seed: the primary solid seed is prepared as a solution of the primary solid seed, which is inoculated into a solid culture medium, and cultured; or a primary liquid seed solution is inoculated into a solid culture medium and cultured;

so that a secondary solid seed is obtained;

(4) enlarging culture of the secondary solid seed in a fermentor; the secondary solid seed is prepared as a solution of the secondary solid seed, which is inoculated into a liquid culture medium in a fermentor for enlarging culture;

(5) collection of cells after fermentation and extraction of DHA.

According to a method of any one of the first aspect of the invention, wherein the *Schizochytrium* is the *Schizochytrium* known in the art. In an embodiment of the invention, the *Schizochytrium* is selected from *Schizochytrium* sp.; and in an embodiment of the invention, the *Schizochytrium* sp. is selected from *Schizochytrium* sp. KDW-12. *Schizochytrium* sp. S31, *Schizochytrium aggregatum* and *Schizochytrium* sp. S8, wherein the *Schizochytrium* sp. KDW-12 was deposited in China General Microbiological Culture Collection Center (address: Datun Road, Chaoyang District, Beijing, Institute of Microbiology, Chinese Academy of Sciences, postal code; 100101) with a deposition number of CGMCC No. 6843.

According to a method of any one of the first aspect of the invention, wherein step (1) is characterized by one or more of the following items:

a. the culture temperature is 25-28° C. and the culture is performed till the cell concentration and the cell morphology are good, for example, the culture time is 2-3 days;

b. the cell concentration of the suspension of the strain is $1.0$-$2.5 \times 10^6$/mL.

According to a method of any one of the first aspect of the invention, wherein step (2) is characterized by one or more of the following items:

a. the inoculation amount is 0.5-2%;

b. the culture temperature is 25-28° C., and the culture is performed till the cell concentration and cell morphology are good, for example, the culture time is 20-28 h;

c. the shaking speed of the liquid culture (for example, shake-flask culture) is 180-220 rpm.

According to a method of any one of the first aspect of the invention, wherein step (3) is characterized by one or more of the following items:

a. the cell concentration of the solution of the primary solid seed is $1.0$-$2.5 \times 10^6$/mL;

b. the solution of the primary solid seed is inoculated into the solid culture medium in an inoculation amount of 0%-20% in volume/weight fraction;

c. the primary liquid seed is inoculated into the solid culture medium in an inoculation amount of 8%-15% in volume/weight fraction; and d. the culture temperature is 25-28° C., the culture is performed till the cell concentration and cell morphology are good, for example, the culture time is 2-3 days.

According to a method of any one of the first aspect of the invention, wherein step (4) is characterized by one or more of the following items:

a. the solution of the secondary solid seed is inoculated into the fermentor for enlarging culture in an inoculation amount of 10%-20% in volume fraction;

b. at the first 48 h of the fermentation, the temperature is controlled at 25-28° C. and the dissolved oxygen is kept at 30%-50% by regulating the shaking speed;

c. from the $48^{th}$ hour to the end of the fermentation, the temperature is controlled at 18-22° C. and the dissolved oxygen is kept at 8%-12% by regulating the shaking speed;

d. the fermentation is terminated when the cell begin to autolyze and the dry cell weight and the yield of DHA are not increased, increased slowly or in a descending trend, for example, the fermentation is carried out for 3-5 days;

e) the pH of fermentation broth is controlled at 6.0-6.5 with ammonia during the fermentation;

f) the concentration of glucose is controlled at 4-8 g/L via automatic feeding of glucose solution during the fermentation.

In an embodiment of the invention, the concentration of the ammonia is 28%.

In an embodiment of the invention, the concentration of the glucose solution is 580 g/L.

According to a method of any one of the first aspect of the invention, the slant culture medium in step (1) contains 20-30 g/L of glucose, 10-15 g/L of peptone, 3-5 g/L of yeast powder, 15-20 g/L of sea crystal and 15-25 g/L of agar powder, with a pH value of 6.0-7.0.

According to a method of any one of the first aspect of the invention, the solid culture medium in step (2) or step (3) comprises a solid component and a liquid component of nutrient solution, wherein the solid component is cereal, the content is 250-400 g/L, the cereal is selected from at least one of rice, wheat and corn, the rice is selected from at least one of rice, millet, unpolished rice and etc., and the wheat is selected from at least one of barley, wheat and oat;

the liquid component of nutrient solution comprises component 1 and component 2, wherein the component 1 comprises 2-5 g/L of glucose, 0.2-0.6 g/L of magnesium sulfate heptahydrate, 1.0-5.0 g/L of dipotassium hydrogen phosphate, 0.1-0.8 g/L of sea salt, 0.2-0.6 g/L of glycine, 1.5-1.8 g/L of threonine, 2-3.5 g/L of methionine and 3-6 g/L of malic acid, water is added to a metered volume, and the pH value is adjusted to 6-7; and the component 2 comprises 10-15 mg/L of $La^{3+}$, 1-4 mg/L of $Ce^{3+}$, 2-6 mg/L of $Sm^{3+}$, 8-12 mg/L of $Nd^{3+}$, 0.6-1.2 mg/L of $Mn^{2+}$, 0.05-0.1 mg/L of $Co^{2+}$, 0.2-0.6 mg/L of biotin, 0.1-0.3 mg/L of cerulenin, 2-5 mg/L of gibberellin GA, 0.5-1.0 mg/L of $VB_{12}$, 0.01-0.05 mg/L of folic acid and the balance of water;

the preparation method of the solid culture medium comprises: the solid component and component 1 of the liquid component of nutrient solution are uniformly mixed, the cereal is steamed or boiled till no white cores exist at the centers of the cereal and the water content is 50%-65% to obtain a raw material of the solid culture medium; the raw material of the solid culture medium and component 2 of the liquid component of nutrient solution are uniformly mixed, and the mixture is loaded with a thickness of 0.2-1.0 cm into a solid fermentation bottle, sterilized to get the solid culture medium;

preferably, the weight/volume ratio of the solid component to component 1 of the liquid component of nutrient solution is (5-10) g:(2-5) mL, the weight/volume ratio of the raw material of the solid culture medium to component 2 of the liquid component of nutrient solution is (10-15) g:(3-6) mL, wherein the solid component is calculated by weight and the liquid component of nutrient solution is calculated by volume.

According to a method of any one of the first aspect of the invention, in step 2), the liquid seed culture medium contains 20-25 g/L of glucose, 20-25 g/L of sodium chloride, 0.2-0.5 g/L of potassium dihydrogen phosphate, 3-5 g/L of yeast powder, 8-12 g/L of magnesium sulfate heptahydrate, 0.1-0.8 g/L of sea salt and 0.2-0.6 g/L of glutamic acid, with a pH value of 6.0-7.0.

According to a method of any one of the first aspect of the invention, the liquid culture medium in the fermentor in step (4) contains 30-60 g/L of glucose, 15-20 g/L of NaCl, 4-8 g/L of $MgSO_4.7H_2O$, 3-8 g/L of yeast powder, 0.5-1.0 g/L of $KH_2PO_4$, 0.2-0.5 g/L of $(NH_4)_2SO_4$, 0.8-1.2 g/L of $NaHCO_3$, 1.0-2.0 μg/L of $CoCl_2$, 0.5-1.0 μg/L of $MnSO_4$, 0.05-0.1 mg/L of $VB_1$ and 0.001-0.01 mg/L of $VB_{12}$, with an initial pH value of 6.0-7.0.

The second aspect of the invention relates to a culture medium used to culture *Schizochytrium* for fermentation production of DHA, which is selected from one or more of the following culture medium:

1) a slant culture medium, containing 20-30 g/L of glucose, 10-15 g/L of peptone, 3-5 g/L of yeast powder, 15-20 g/L of sea crystal and 15-25 g/L of agar powder, with a pH value of 6.0-7.0;

2) a solid culture medium, containing a solid component and a liquid component of nutrient solution, wherein the solid component is cereal with an amount of 250-400 g/L, the cereal is selected from at least one of rice, wheat and corn, the rice is selected from at least one of rice, millet, unpolished rice and etc., and the wheat is selected from at least one of barley, wheat and oat;

the liquid component of nutrient solution comprises component 1 and component 2, the component 1 comprises 2-5 g/L of glucose, 0.2-0.6 g/L of magnesium sulfate heptahydrate, 1.0-5.0 g/L of dipotassium hydrogen phosphate, 0.1-0.8 g/L of sea salt, 0.2-0.6 g/L of glycine, 1.5-1.8 g/L of threonine, 2-3.5 g/L of methionine and 3-6 g/L of malic acid, water is added to a metered volume, and the pH value is adjusted to 6-7; and the component 2 comprises 10-15 mg/L of $La^{3+}$, 1-4 mg/L of $Ce^{3+}$, 2-6 mg/L of $Sm^{3+}$, 8-12 mg/L, of $Nd^{3+}$, 0.6-1.2 mg/L of $Mn^{2+}$, 0.05-0.1 mg/L of $Co^{2+}$, 0.2-0.6 mg/L of biotin, 0.1-0.3 mg/L of cerulenin, 2-5 mg/L of gibberellin GA, 0.5-1.0 mg/L of $VB_{12}$, 0.01-0.05 mg/L of folic acid and the balance of water;

the preparation method of the solid culture medium comprises: the solid component and component 1 of the liquid component of nutrient solution are uniformly mixed, the cereal is steamed or boiled till no white cores exist at the centers of the cereal and the water content is 50%-65% to obtain a raw material of the solid culture medium; the raw material of the solid culture medium and component 2 of the liquid component of nutrient solution are uniformly mixed, and the mixture is loaded with a thickness of 0.2-1.0 cm into a solid fermentation bottle, and sterilized to obtain the solid culture medium;

preferably, the weight/volume ratio of the solid component to component 1 of the liquid component of nutrient solution is (5-10) g:(2-5) mL, the weight/volume ratio of the raw material of the solid culture medium to component 2 of the liquid component of nutrient solution is (10-15) g:(3-6) mL, wherein the solid component is calculated by weight and the liquid component of nutrient solution is calculated by volume;

3) a liquid seed culture medium, containing 20-25 g/L of glucose, 20-25 g/L of sodium chloride, 0.2-0.50 g/L of potassium dihydrogen phosphate, 3-5 g/L of yeast powder, 8-12 g/L of magnesium sulfate heptahydrate, 0.1-0.8 g/L of sea salt and 0.2-0.6 g/L of glutamic acid, with a pH value of 6.0-7.0;

4) a liquid culture medium in a fermentor, containing 30-60 g/L of glucose, 15-20 g/L of NaCl, 4-8 g/L of $MgSO_4 \cdot 7H_2O$, 3-8 g/L of yeast powder, 0.5-1.0 g/L of $KH_2PO_4$, 0.2-0.5 g/L of $(NH_4)_2SO_4$, 0.8-1.2 g/L of $NaHCO_3$, 1.0-2.0 µg/L of $CoCl_2$, 0.5-1.0 µg/L of $MnSO_4$, 0.05-0.1 mg/L of $VB_1$ and 0.001-0.01 mg/L of $VB_{12}$, with an initial pH of 6.0-7.0.

The invention further relates to a method for producing DHA through solid culture and liquid fermentation of *Schizochytrium*, which is characterized in that, the method comprising the following steps:

1) activation of a strain and preparation of a suspension of the strain: a *Schizochytrium* strain is inoculated into a slant culture medium, cultured and activated, and when the culture period expires, the slant is added with 0.85% saline to wash strain to obtain the suspension of the strain;

2) preparation of a primary seed: the suspension of the strain obtained in step 1) is inoculated into a solid culture medium in an inoculation amount of 1% in weight fraction and cultured to obtain a primary solid seed; or the suspension of the strain obtained in step 1) is inoculated into a liquid seed culture medium in an inoculation amount of 1% in volume fraction and shake-flask cultured to obtain a primary liquid seed;

3) preparation of a secondary solid seed: the primary solid seed is added with 0.85% saline in a ratio of 1:1 (W/V) to wash the strain to obtain a suspension of the strain;

under sterile conditions:

the primary solid seed solution is inoculated into a solid culture medium in an inoculation amount of 10%-20% in volume/weight fraction; or the primary liquid seed is inoculated into a solid culture medium in an inoculation amount of 8%-15% in volume/weight fraction, uniformly mixed by shaking the solid fermentation bottle, and cultured at 25-28° C. for 2-3 days;

so that the secondary solid seed is obtained;

4) enlarging culture of the secondary solid seed in a fermentor; the secondary solid seed is added with sterile water in a ratio of 1:(3-5) (W/V) and oscillated to wash off the strain, an obtained suspension of the strain is inoculated into a fermentor in an inoculation amount of 10%-20% in volume fraction for enlarging culture, at the first 48 h, the temperature is controlled at 25-28° C., the dissolved oxygen is kept at 30%-50% by regulating the shaking speed, and the temperature is controlled at 18-22° C. from the $48^{th}$ hour to the and of fermentation, and the fermentation is carried out for 3-5 days, the fermentation pH is controlled at 6.0-6.5 with 28% ammonia in a weight percentage, the concentration of glucose is controlled at 4-8 g/L in the whole fermentation process via automatic feeding of 580 g/L of glucose solution which is sterilized at 118° C. for 25 min;

5) collection of cells after fermentation and extraction of DHA oil.

In an embodiment of the invention, in step 1), the formula of the slant culture medium is as follows: 20-30 g/L of glucose, 10-15 g/L of peptone, 3-5 g/L of yeast powder, 15-20 g/L of sea crystal and 15-25 g/L (such as 20 g/L) of agar powder, with a pH value of 6-7, and sterilized at 121° C. for 30 min; the culture and activation temperature is 25-28° C., the culture and activation time is 2-3 days, and the cell concentration of the suspension of the strain is $1.0-2.5 \times 10^6$/mL.

In an embodiment of the invention, in step 2), the solid culture medium comprises a solid component and a liquid component of nutrient solution, wherein the solid component is cereal with an amount of 250-400 g/L, the cereal is selected from at least one of rice, wheat and corn, the rice is selected from at least one of rice, millet, unpolished rice and etc., and the wheat is selected from at least one of barley, wheat and oat.

In an embodiment of the invention, in step 2), the liquid component of nutrient solution comprises component 1 and component 2, wherein the component 1 comprises 2-5 g/L of glucose, 0.2-0.6 g/L of magnesium sulfate heptahydrate, 1.0-5.0 g/L of dipotassium hydrogen phosphate, 0.1-0.8 g/L of sea salt, 0.2-0.6 g/L of glycine, 1.5-1.8 g/L of threonine, 2-3.5 g/L of methionine and 3-6 g/L of malic acid, water is added to a metered volume, and the pH value is adjusted to 6-7; and the component 2 comprises 10-15 mg/L of $La^{3+}$, 1-4 mg/L of $Ce^{3+}$, 2-6 mg/L of $Sm^{3+}$, 8-12 mg/L of $Nd^{3+}$, 0.6-1.2 mg/L of $Mn^{2+}$, 0.05-0.1 mg/L of $Co^{2+}$, 0.2-0.6 mg/L of biotin, 0.1-0.3 mg/L of cerulenin, 2-5 mg/L of gibberellin GA, 0.5-1.0 mg/L of $VB_{12}$, 0.01-0.05 mg/L of folic acid and the balance of water.

In an embodiment of the invention, the preparation method of the solid culture medium in step 2) comprises: the solid component and component 1 of the liquid component of nutrient solution are uniformly mixed, the cereal is steamed or boiled till no white cores exist at the centers of the cereals and the water content is 50%-65% to obtain a raw material of the solid culture medium; the raw material of the solid culture medium and component 2 of the liquid component of nutrient solution are uniformly mixed, and the mixture is loaded with a thickness of 0.2-1.0 cm into a K solid fermentation bottle, sterilized at 121° C. for 30 min to prepare the solid culture medium.

In an embodiment of the invention, the weight/volume ratio of the solid component to component 1 of the liquid component of nutrient solution is (5-10) g:(2-5) mL, wherein the solid component is calculated by weight and component 1 of the liquid component of nutrient solution is calculated by volume;

the weight/volume ratio of the raw material of the solid culture medium to component 2 of the liquid component nutrient solution is (10-15) g:(3-6) mL, wherein the raw material of the solid culture medium is calculated by weight and component 2 of the liquid component nutrient solution is calculated by volume.

In an embodiment of the invention, in step 2), the liquid seed culture medium contains 20-25 g/L of glucose, 20-25 g/L of sodium chloride, 0.2-0.5 g/L of potassium dihydrogen phosphate, 3-5 g/L of yeast powder, 8-12 g/L of magnesium sulfate heptahydrate, 0.1-0.8 g/L of sea salt and 0.2-0.6 g/L of glutamic acid, with a pH value of 6-7, and sterilized at 121° C. for 30 min.

In an embodiment of the invention, in step 2), the culture temperature is 25-28° C. and the culture time is 1 day.

In an embodiment of the invention, in step 2), the shaking speed of the shake flask is 180-220 rpm, the temperature of the shake-flask culture is 25-28° C., and the shake-flask culture time is 1 day.

In an embodiment of the invention, the liquid fermentation culture medium used for enlarging culture in step 4) comprises 30-60 g/L of glucose, 15-20 g/L of NaCl, 4-8 g/L of $MgSO_4.7H_2O$, 3-8 g/L of yeast powder, 0.5-1.0 g/L of $KH_2PO_4$, 0.2-0.5 g/L of $(NH_4)_2SO_4$, 0.8-1.2 g/L of $NaHCO_3$, 1.0-2.0 μg/L of $CoCl_2$, 0.5-1.0 μg/L of $MnSO_4$, 0.05-0.1 mg/L of $VB_1$ and 0.001-0.01 mg/L of $VB_{12}$, with an initial pH of 6.0-7.0; it is optimal to maintain 8%-12% of dissolved oxygen for fermentation.

In a specific embodiment of the invention, a method for producing DHA through solid culture and liquid fermentation of *Schizochytrium* comprises the following steps:

1) activation of a strain and preparation of a suspension of the strain: the *Schizochytrium* strain is inoculated into a slant culture medium, cultured and activated, and when the culture period expires, the slant is added with sterile water or an isotonic saline solution (for example, 0.85%-0.9% saline) to wash the strain and obtain the suspension of the strain;

in step 1), the formula of the slant culture medium is as follows: 20-30 g/L of glucose, 10-15 g/L of peptone, 3-5 g/L of yeast powder, 15-20 g/L of sea crystal and 15-25 g/L of agar powder, with a pH value of 6-7, and sterilized (for example, at 121° C. for 30 min); the culture and activation temperature is 25-28° C., the culture and activation time is 2-3 days, and the cell concentration of the suspension of the strain is $1.0-2.5×10^6$/mL;

2) preparation of a primary seed: the suspension of the strain obtained in step 1) is inoculated into a solid culture medium (for example, in an inoculation amount of 0.5-2% or 1% in a weight fraction) and cultured to obtain a primary solid seed; or the suspension of the strain obtained in step 1) is inoculated into a liquid seed culture medium (for example, in an inoculation amount of 0.5-2% or 1% in a weight fraction) and shake-flask cultured to obtain a primary liquid seed;

in step 2), the solid culture medium comprises a solid component and a liquid component of nutrient solution, wherein the solid component is cereal with an amount of 250-400 g/L, the cereal is selected from at least one of rice, wheat and corn, the rice is selected from at least one of rice, millet, unpolished rice and etc., and the wheat is selected from at least one of barley, wheat and oat;

the liquid component of nutrient solution comprises component 1 and component 2, wherein the component 1 comprises 2-5 g/L of glucose, 0.2-0.6 g/L of magnesium sulfate heptahydrate, 1.0-5.0 g/L of dipotassium hydrogen phosphate, 0.1-0.8 g/L of sea salt, 0.2-0.60 g/L of glycine, 1.5-1.8 g/L of threonine, 2-3.5 g/L of methionine and 3-6 g/L of malic acid, water is added to a metered volume, and the pH value is adjusted to 6-7; the component 2 comprises 10-15 mg/L of $La^{3+}$, 1-4 mg/L of $Ce^{3+}$, 2-6 mg/L of $Sm^{3+}$, 8-12 mg/L of $Nd^{3+}$, 0.6-1.2 mg/L of $Mn^{2+}$, 0.05-0.1 mg/L of $Co^{2+}$, 0.2-0.6 mg/L of biotin, 0.1-0.3 mg/L of cerulenin, 2-5 mg/L of gibberellin GA, 0.5-1.0 mg/L of $VB_{12}$, 0.01-0.05 mg/L of folic acid and the balance of water;

the preparation method of the solid culture medium comprises: the solid component and component 1 of the liquid component of nutrient solution are uniformly mixed, the cereal is steamed or boiled till no white cores exist at the centers of the cereal and the water content is 50%-65%, to obtain a raw material of the solid culture medium; the raw material of the solid culture medium and component 2 of the liquid component of nutrient solution are uniformly mixed, the mixture is loaded with a thickness of 0.2-1.0 cm into a K solid fermentation bottle, and is subpackaged in 150-2500 g/bottle into a 1 L-10 L of solid fermentation bottle, sterilized at 121° C. for 30 min to prepare the solid culture medium;

the weight/volume ratio of the solid component to component 1 of the liquid component of nutrient solution is (5-10) g:(2-5) mL, wherein the solid component is calculated by weight and component 1 of the liquid component of nutrient solution is calculated by volume;

the weight/volume ratio of the raw material of the solid culture medium to component 2 of the liquid component of nutrient solution is (10-15) g:(3-6) mL, wherein the raw material of the solid culture medium is calculated by weight and component 2 of the liquid component of nutrient solution is calculated by volume;

the liquid seed culture medium comprises 20-25 g/L of glucose, 20-25 g/L of sodium chloride, 0.2-0.5 g/L of potassium dihydrogen phosphate, 3-5 g/L of yeast powder, 8-12 g/L of magnesium sulfate heptahydrate, 0.1-0.8 g/L of sea salt and 0.2-0.6 g/L of glutamic acid, with a pH value of 6-7, and sterilized (for example, sterilized at 121° C. for 30 min);

the culture temperature is 25-28° C., the culture is performed till the cell concentration and cell morphology are good, for example, the culture time is 20-28 h (for example, about 1 day); the shaking speed of the shake flask is 180-220 rpm; and the temperature of the shake-flask culture is 25-28° C., the culture is performed till the cell concentration and the cell morphology are good, for example, the shake-flask culture time is 20-28 h (for example, about 1 day);

3) preparation of a secondary solid seed: the primary solid seed is added with sterile water or isotonic saline solution (e.g. 0.85% saline) to wash the strain (for example, according to a ratio of 1:1 (W/V)) to obtain a suspension of the strain;

under sterile conditions:

the primary solid seed solution is inoculated into a solid culture medium in an inoculation amount of 10%-20% in volume/weight fraction; or the primary liquid seed is inoculated into a solid culture medium in an inoculation amount of 8%-15% in volume/weight fraction;

uniformly mixed by shaking the K bottle, and cultured at 25-28° C. till the cell concentration and the cell morphology are good, for example, cultured for 2-3 days;

so that a secondary solid seed is prepared;

4) enlarging culture of the secondary solid seed in a fermentor: the secondary solid seed is added with sterile water in a ratio of 1:(3-5) (W/V) and oscillated to wash off the strain, an obtained suspension of the strain is inoculated into a fermentor in an inoculation amount of 10%-20% in volume fraction for enlarging culture, at the first 48 h of fermentation, the temperature is controlled at 25-28° C. and the dissolved oxygen is kept at 30%-50% by regulating the shaking speed, and the temperature is controlled at 18-22° C. from the $48^{th}$ hour to the end of the fermentation, the fermentation is terminated when the cell begin to autolyze, the dry cell weight and the yield of the DHA are not increased, increased slowly or in a descending trend, for example, fermenting for 3-5 days, the fermentation pH is controlled at 6.0-6.5 with ammonia (such as 28% ammonia), and the concentration of glucose is controlled at 4-8 g/via automatic feeding of a glucose solution (for example, the glucose solution with the concentration of 580 g/L, and sterilized at 118° C. for 25 min) in the whole fermentation process;

in step 4), the liquid fermentation culture medium using for enlarging culture comprises 30-60 g/L of glucose, 15-20 g/L of NaCl, 4-8 g/L of $MgSO_4 \cdot 7H_2O$, 3-8 g/L of yeast powder, 0.5-1.0 g/L of $KH_2PO_4$, 0.2-0.5 g/L of $(NH_4)_2SO_4$, 0.8-1.2 g/L of $NaHCO_3$, 1.0-2.0 µg/L of $CoCl_2$, 0.5-1.0 µg/L of $MnSO_4$, 0.05-0.1 mg/L of $VB_1$ and 0.001-0.01 mg/L of $VB_{12}$, with an initial pH of 6.0-7.0; and it is optimal to maintain the dissolved oxygen during fermentation at 8%-12%;

5) collection of cells after the fermentation and extraction of DHA.

In an embodiment of the invention, the dry cell weight in fermentation broth is determined and reaches 105-160 g/L and the content of the DHA reaches 20-35 g/L.

In the invention, the *Schizochytrium* can be any *Schizochytrium* known in the art, such as *Schizochytrium* strains obtained from American Type Culture Collection, Institute for Fermentation, Osaka, Japan and other collection institutions. In the embodiments of the invention, the *Schizochytrium* is *Schizochytrium* sp., the *Schizochytrium* sp. for example can be *Schizochytrium* sp. KDW-12, S31, S8 or *Schizochytrium aggregatum*.

The *Schizochytrium* sp. KDW-12 used in the invention was deposited in China General Microbiological Culture Collection Center (address: Datun Road, Chaoyang District, Beijing, Institute of Microbiology, Chinese Academy of Sciences, postal code: 100101) with a deposition number of CGMCC No, 6843 on Nov. 20, 2012.

In an embodiment of the invention, the isotonic saline solution is saline, namely 0.85-0.9% sodium chloride solution.

In the invention, the culture time on the secondary solid seed and each phase in the early stage of fermentation is determined according to an optimization experiment developed previously for optimizing culture time, good cell concentration and cell morphology can be obtained in the selected culture time; the indexes to terminate the fermentation in the fermentor include that the cell begin to autolyze, the dry cell weight and the yield of DHA are not increased, increased slowly or in a descending trend.

In the invention, the control of ammonia and glucose are the known prior arts, namely the control of the pH with ammonia is mainly realized by setting a control value through an automatic control system on the fermentor, and when the value is lower than the set value, a peristaltic pump would automatic feeding of ammonia for adjustment; the control of the glucose is similar to the control of ammonia, that is, a sample is taken each time, the concentration of remaining sugar is determined by a biosensing analyzer, the volume of glucose which needs to be supplemented is calculated according to a set control point, the corresponding opening degree and the period are set in the automatic control system and automatic adjusted via the peristaltic pump.

In the invention, for the culture time, 1 day is not limited to accurate 24 h, for example, could be about 20-28 h, 22-26 h or 24 h.

In the invention, a method for preparing corresponding seed solution from a strain after activation or a primary or a secondary solid seed is as follows: for the strain after activation and the primary solid seed, the sterile water or isotonic saline solution, such as 0.85%-0.9% sodium chloride solution, can be added to wash the strain to prepare a suspension of the strain; for the secondary solid seed, the sterile water can be added to prepare a suspension of the strain; the suspension of the strain is the corresponding seed solution; and the cell concentration of the suspension of the strain can be $1.0$-$2.5 \times 10^6$/mL.

In the invention, both of the weight in weight/volume percent in preparation of suspension of the strain or seed solution and the weight in volume/weight percent in inoculation refer to the weight of solid culture medium.

ADVANTAGEOUS EFFECTS OF THE INVENTION

The invention abandons the traditional seed culture process, directly performs liquid fermentation culture using the seed solution obtained from the solid fermentation: slant activation, primary solid seed/shake flask liquid seed preparation, secondary solid seed solution preparation and liquid fermentation. In the invention, the seed preparation method is improved, the seed enlarging technology is simplified, the period of seed culture and fermentation is shortened, therefore the investment is reduced and the cost is saved and the method in the invention is more suitable for large-scale production; in addition, the solid culture medium is of eutrophy, is rich in a plurality of growth factors, and is more beneficial to the growth of the seeds; cells are growing strong in viability and good in synchronism in solid culture medium; besides, there are less waste water and less waste residue which are generated in the stage of the solid seeds culture, and has less environmental pollution.

The invention overcomes the defect in traditional fermentation method that there are many stages of seed enlarging culture and simplifies the technological process of producing DHA through improving the preparation of the seed solution used for fermentation of DHA; the solid culture medium is of eutrophy, the seeds are full grown and strong in viability, therefore the lag phase after loading the seeds into the tank is shortened, the yield of DHA is increased, the production cost is reduced and the stable production capacity is kept; there are less waste water and less waste residue which are generated in the stage of the solid seed culture, and has less environmental pollution; and the DHA obtained through fermentation can be used as a nutrient supplement to provide the long-chain polyunsaturated fatty acid required by human and animals.

SPECIFIC MODE FOR CARRYING OUT THE INVENTION

The embodiments of the invention are described in detail by combining the following examples. However, a person skilled in the art would understand that the following examples are only used to illustrate the invention rather than defining the scope of the invention. When no particular conditions are specified in the examples, the examples are carried out under conventional conditions or the conditions recommended by the manufacturer. The agents or instruments, whose manufacturers are not indicated, are conventional products that are available commercially.

Strains used in the embodiments are as follows:
*Schizochytrium* sp, KDW-12, which was deposited in China General Microbiological Culture Collection Center (address: Datun Road, Chaoyang District, Beijing, Institute of Microbiology, Chinese Academy of Sciences, postal code: 100101) with a deposition number of CGMCC No. 6843 on Nov. 20, 2012.
*Schizochytrium* sp. S31 (ATCC No. 20888)
*Schizochytrium* sp, S8 (ATCC No. 20880)
*Schizochytrium aggregatum* (ATCC No. 28209)

Example 1

The *Schizochytrium* sp. KDW-12 strain was inoculated into a slant culture medium and cultured for activation, the temperature was 25° C., and the culture was performed for 2 days. The formula of the slant culture medium is as follows: 20 g/L of glucose, 15 g/L of peptone, 3 g/L of yeast powder, 15 g/L of sea crystal (sea salt) and 20 g/L of agar powder, with a pH value of 6.5, sterilized at 121° C. for 30 min. When the culture period expired, the slant was added with 0.85% saline to wash strain, a suspension of the strain was obtained and the cell concentration was controlled at $2.5 \times 10^6$/mL.

The obtained suspension of the strain was directly inoculated into a sterilized solid culture medium (the loading amount of solid culture medium was 150 g/bottle subpackaged in 1000 ml of K bottle) in an inoculation amount of 1% in volume/weight fraction (V/W, the volume of the suspension of the strain/the weight of the solid culture medium), cultured at 25° C. for 1 day, and the K bottle was snaked once every 8-12 h during the culture period to uniformly mix so as to benefit the seed to make full use of the nutrient to grow. Then the primary solid seed was prepared.

Under sterile conditions, the primary solid seed (the primary solid seed used for inoculation was added with 0.85% saline in a ratio of 1:1 (W/V) to wash the strain, the suspension of the strain was prepared and the cell concentration is controlled at $1.0 \times 10^6$/mL) was inoculated into a solid culture medium (the secondary solid culture medium was 150 g/bottle subpackaged in 1000 ml K bottle) in an inoculation amount of 10% in volume/weight fraction (V/W), the K bottle was shaked and uniformly mixed, cultured at 25° C. for 2.5 days, and the K bottle was shaked once every 8-12 h during the culture to uniformly mix so as to benefit the seed to make full use of the nutrient to grow. The secondary solid seed was prepared.

The secondary solid seed was added sterile water in a ratio of 1:4 (W/V), oscillated to wash off the strain, and the cell concentration was controlled at $1.5 \times 10^6$/mL. An obtained suspension of the strain was inoculated into a 50 L fermentor in an inoculation amount of 15% in volume fraction for enlarging culture, and the volume after inoculation was 32 L. At the first 48 h of fermentation, the temperature was controlled at 25° C., the dissolved oxygen was kept at 40% by regulating the shaking speed and the ventilation, and from the 48$^{th}$ hour to the end of fermentation, the temperature was controlled at 22° C., the dissolved oxygen was kept at about 10%. The sample was taken once every 8 h during the fermentation process to determine the residual sugar, the cell concentration, the dry cell weight and the content of DHA in fermentation broth, and the fermentation lasted for 4 days, when the cell begin to autolyze, the dry cell weight and the yield of DHA were not increased, increased slowly or in a descending trend. The fermentation pH was controlled at 6.5 with 28% ammonia in weight percentage, and the concentration of glucose was controlled at 8 g/L via automatic feeding of 580 g/L of glucose solution which is sterilized at 118° C. for 25 min in the whole fermentation process.

A preparation method of the solid culture medium is: the solid culture medium consists of a solid component and a liquid component of nutrient solution, wherein the solid component was millet, and the content was 375 g/L (the weight of the solid component/the volume of the liquid component of nutrient solution). The millet and component 1 of the liquid component of nutrient solution were uniformly mixed in a ratio of 8:3 (W/V), the cereal was steamed or boiled till no white cores existed at the centers of the cereal and the water content was 55%, and a raw material of the solid culture medium was obtained. The raw material of the solid culture medium and component 2 of the liquid component of nutrient solution were uniformly mixed in a ratio of 10:3 (W/V), the mixture was loaded with a thickness of 0.3 cm into a K solid fermentation bottle, and subpackaged with a loading amount of 150 g/bottle into 1000 ml of K bottle, sterilized at 121° C. for 30 min, and the solid culture medium was prepared.

Component 1 of the liquid component nutrient solution comprised 3 g/L of glucose, 0.2 g/L of magnesium sulfate heptahydrate, 3.0 g/L of dipotassium hydrogen phosphate, 0.6 g/L of sea salt, 0.6 g/L of glycine, 1.5 g/L of threonine, 2 g/L of methionine, 4 g/L of malic acid, water was added to a required volume, and the pH value was adjusted to 6.5. The component 2 comprised 15 mg/L of $La^{3+}$, 2 mg/L of $Ce^{3+}$, 3 mg/L of $Sm^{3+}$, 8 mg/L of $Nd^{3+}$, 1.0 mg/L of $Mn^{2+}$, 0.08 mg/L of $Co^{2+}$, 0.2 mg/L of biotin, 0.1 mg/L of cerulenin, 5 mg/L of gibberellin GA, 1.0 mg/L of $VB_{12}$, 0.03 mg/L of folic acid and the balance of water.

The liquid fermentation culture medium comprised 30 g/L of glucose, 20 g/L of NaCl, 5 g/L of $MgSO_4.7H_2O$, 3 g/L of yeast powder, 1.0 g/L of $KH_2PO_4$, 0.4 g/L of $(NH_4)_2SO_4$, 1.2 g/L of $NaHCO_3$, 2.0 μg/L of $CoCl_2$, 0.7 μg/L of $MnSO_4$, 0.06 mg/L of $VB_1$ and 0.005 mg/L of $VB_{12}$, with an initial pH of 6.5. The initial pH referred to, after the preparation of the culture medium, the pH obtained by adjustment with a pH meter before sterilization.

The cells were centrifugated and collected after the fermentation, the dry cell weight in fermentation broth was determined and reached 125 g/L, and gas chromatography detection showed the content of DHA reached 25 g/L. The methods of treatment of the fermentation broth and the extraction and determination of DHA were referenced to the methods disclosed in Chinese patent CN101638361A. The extracted DHA can be used as a nutritional supplement to provide the long-chain polyunsaturated fatty acid required by human and animals.

Example 2

The *Schizochytrium* sp. KDW-12 strain was inoculated into a slant culture medium, cultured and activated at 28° C., and cultured for 2 days. The formula of the slant culture medium was as follows: 25 g/L of glucose, 12 g/L of peptone, 3 g/L of yeast powder, 16 g/L of sea crystal and 20 g/L of agar powder, with pH value of 6.0, sterilized at 121° C. for 30 min. When a culture period expired, the slant was added with 0.85% saline to wash the strain, a suspension of the strain was obtained, and the cell concentration was controlled at $1.0 \times 10^6$/mL.

The obtained suspension of the strain was directly inoculated into a shake flask liquid culture medium (150 ml liquid medium in a 500 ml flask) with an inoculation amount of 1%, with shake flask shaking speed of 220 rpm, and cultured at 28° C. for 1 day, and the primary liquid seed was prepared. The shake flask liquid seed culture medium comprised 25 g/L of glucose, 20 g/L of sodium chloride, 0.2 g/L of potassium dihydrogen phosphate, 5 g/L of yeast powder, of magnesium sulfate heptahydrate, 0.4 g/L of sea salt and 0.4 g/L of glutamic acid, with pH value of 6.0, sterilized at 121° C. for 30 min.

Under sterile conditions, the primary liquid seed was inoculated into the solid culture medium (the loading amount was 250 g/bottle subpackaged in 1000 ml of K bottle) in an inoculation amount of 10% in volume/weight fraction, the K bottle was shaked and uniformly mixed, cultured at 26° C. for 3 days, and the K bottle was stoked once every 8-12 h during the culture to uniformly mix so as to benefit the seed to make full use of the nutrient to grow. The secondary solid seed was prepared.

The secondary solid seed was added sterile water in a ratio of 1:3 (W/V), oscillated to wash off the strain, and the cell concentration was controlled at $2.5 \times 10^6$/mL. An obtained suspension of the strain was inoculated into a 100 L fermentor in an inoculation amount of 20% in volume/weight fraction for enlarging culture, and the volume after inoculation was 60 L. At the first 48 h of fermentation, the temperature was controlled at 28° C., the dissolved oxygen was kept at 30% by regulating shaking speed and the ventilation, and from the $48^{th}$ hour to the end of the fermentation, the temperature was controlled at 18° C., the dissolved oxygen was maintained at about 10%. The sample was taken once every 8 h during the fermentation process to determine the residual sugar, the cell concentration, the dry cell weight and the content of DHA in fermentation broth, and the fermentation lasted for 5 days, when the cell begin to autolyze, the dry cell weight of strain and the yield of DHA were not increased, increased slowly or in a descending trend. The fermentation pH was controlled at 6.0 with 28% ammonia in weight percentage, and the concentration of glucose was controlled at 7 g/L via automatic feeding of 580 g/L of glucose solution which was sterilized at 118° C. for 25 min in the whole fermentation process.

A preparation method of the solid culture medium was: the solid culture medium consisted of solid component and liquid component of nutrient solution, wherein the solid component was millet with an amount of 300 g/L. The millet and component 1 of the liquid component of nutrient solution were uniformly mixed in the ratio of 8:3 (W/V), the cereal was steamed or boiled till no white cores existed at the centers of the cereals and the water content was 60%, and a raw material of the solid culture medium was obtained. The raw material of the solid culture medium and component 2 of the liquid component of nutrient solution were uniformly mixed in the ratio of 10:4 (W/V), the mixture was loaded with a thickness of 0.5 cm into a K solid fermentation bottle, and subpackaged with a loading amount of 250 g/bottle into 1000 ml K bottle, sterilized at 121° C. for 30 min, and the solid culture medium was prepared.

Component 1 of the liquid nutrient solution comprised 5 g/L of glucose, 0.4 g/L of magnesium sulfate heptahydrate, 2.0 g/L of dipotassium hydrogen phosphate, 0.5 g/L of sea salt, 0.3 g/L of glycine, 1.5 g/L of threonine, 3.5 g/L of methionine, 6 g/L of malic acid, water was added to a required volume, and the pH value was adjusted to 6.0. The component 2 comprised 10 mg/L of $La^{3+}$, 4 mg/L of $Ce^{3+}$, 5 mg/L of $Sm^{3+}$, 9 mg/L of $Nd^{3+}$, 0.8 mg/L of $Mn^{2+}$, 0.06 mg/L of $Co^{2+}$, 0.2 mg/L of biotin, 0.1 mg/L of cerulenin, 2 mg/L of gibberellin GA, 0.8 mg/L of $VB_{12}$, 0.03 mg/L of folic acid and the balance of water.

The liquid fermentation culture medium comprised 40 g/L of glucose, 15 g/L of NaCl, 4 g/L of $MgSO_4.7H_2O$, 5 g/L of yeast powder, 0.5 g/L of $KH_2PO_4$, 0.2 g/L of $(NH_4)_2SO_4$, 0.89 g/L of $NaHCO_3$, 1.6 µg/L of $CoCl_2$, 1.0 µg/L of $MnSO_4$, 0.1 mg/L of $VB_1$ and 0.01 mg/L of $VB_{12}$, with an initial pH of 6.0.

The cells were centrifugated and collected after the fermentation, the dry cell weight in the fermentation broth was determined and reached 159 g/L, and gas chromatography showed the content of DHA reached 34.5 g/L. The methods of treatment of the fermentation broth and the extraction and determination of the DHA were referenced to the methods disclosed in Chinese patent CN101638361A. The extracted DHA can be used as a nutrient supplement to provide the long-chain polyunsaturated fatty acid required by human and animals.

Example 3

The *Schizochytrium* sp. KDW-12 strain was inoculated into a slant culture medium, cultured and activated at 28° C., cultured for 3 days. The formula of the slant culture medium was as follows: 30 g/L of glucose, 12 g/L of peptone, 3 g/L of yeast powder, 15 g/L of sea crystal and 20 g/L of agar powder, with pH value of 6.5, sterilized at 121° C. for 30 min. When a culture period expired, the slant was added with 0.85% saline to wash strain, a suspension of the strain was obtained, and the cell concentration was controlled at $2.0 \times 10^6$/mL.

The obtained suspension of the strain was directly inoculated into a shake flask liquid culture medium (150 ml of liquid loading volume in a 500 ml flask) in an inoculation amount of 1%, with shake flask shaking speed of 220 rpm, and cultured at 28° C. for 1 day, and the primary liquid seed was prepared. The shake flask liquid seed culture medium comprised 20 g/L of glucose, 22 g/L of sodium chloride, 0.2 g/L of potassium dihydrogen phosphate, 3 g/L of yeast powder, 10 g/L of magnesium sulfate heptahydrate, 0.3 g/L of sea salt and 0.6 g/L of glutamic acid, with pH value of 6.5, sterilized at 121° C. for 30 min.

Under sterile conditions, the primary liquid seed was inoculated into the solid culture medium (the loading amount was 300 g/bottle subpackaged in 1000 ml of K bottle) in an inoculation amount of 8% in volume/weight fraction, the K bottle was shaked and uniformly mixed, cultured at 26° C. for 3 days, and the K bottle was shaked once every 8-12 h during the culture to uniformly mix so as to benefit the seed to make full use of the nutrient to grow. The secondary solid seed was prepared.

The secondary solid seed was added sterile water in a ratio of 1:3 (W/V), oscillated to wash off the strain, and the cell concentration was controlled at $2.0 \times 10^6$/mL. An obtained suspension of the strain was inoculated into a 100 L fermentor in an inoculation amount of 10% in volume fraction for enlarging culture, and the volume after inoculation was 60 L. At the first 48 h of fermentation, the temperature was controlled at 25° C., the dissolved oxygen was kept at 30% by regulating the shaking speed and the ventilation, and from the $48^{th}$ hour to the end of the fermentation, the temperature was controlled at 20° C. and the dissolved oxygen was maintained at about 10%. The sample was taken once every 8 h during the fermentation process to determine the residual sugar, the cell concentration, the dry cell weight and the content of DHA in fermentation broth, and the fermentation lasted for 5 days, when the cell begin to autolyze, the dry cell weight and the yield of DHA were not increased, increased slowly or in a descending trend. The fermentation pH was controlled at 6.0 with 28% ammonia in weight percentage, and the concentration of glucose was controlled at 8 g/L via automatic feeding of 580 g/L glucose solution which was sterilized at 118° C. for 25 min in the whole fermentation process.

A preparation method of the solid culture medium was: the solid culture medium consisted of a solid component and a liquid component of nutrient solution, wherein the solid component was wheat, and the content was 350 g/L. The wheat and component 1 of the liquid component of nutrient solution were uniformly mixed in a ratio of 10:4 (W/V), the cereal was steamed or boiled till no white cores existed at the centers of the cereals and the water content was 55%, and a raw material of the solid culture medium was obtained. The raw material of the solid culture medium and component 2 of the liquid component of nutrient solution were uniformly mixed in a ratio of 15:4 (W/V), the mixture was loaded with a thickness of 0.7 cm into a K solid fermentation bottle, and subpackaged with a loading amount of 300 g/bottle in 1000 ml K bottle, sterilized at 121° C. for 30 min, and the solid culture medium was prepared.

Component 1 of the liquid nutrient solution comprised 3.5 g/L of glucose, 0.3 g/L of magnesium sulfate heptahydrate, 3.0 g/L of dipotassium hydrogen phosphate, 0.4 g/L of sea salt, 0.5 g/L of glycine, 1.6 g/L of threonine, 3.5 g/L of methionine, 5 g/L of malic acid, water was added to a required volume, and the pH value was adjusted to 6.0. The component 2 comprised 12 mg/L of $La^{3+}$, 4 mg/L of $Ce^{3+}$, 5 mg/L of $Sm^{3+}$, 8 mg/L of $Nd^{3+}$, 0.9 mg/L of $Mn^{2+}$, 0.08 mg/L of $Co^2$, 0.4 mg/L of biotin, 0.1 mg/L of cerulenin, 3 mg/L of gibberellin GA, 0.8 mg/L of $VB_{12}$, 0.02 mg/L of folic acid and the balance of water.

The liquid fermentation culture medium comprised 40 g/L of glucose, 16 g/L of NaCl, 6 g/L of $MgSO_4.7H_2O$, 4 g/L of yeast powder, 1.0 g/L of $KH_2PO_4$, 0.5 g/L of $(NH_4)_2SO_4$, 1.2 g/L of $NaHCO_3$, 2.0 µg/L of $CoCl_2$, 1.0 µg/L of $MnSO_4$, 0.05 mg/L of $VB_1$ and 0.005 mg/L of $VB_{12}$, with an initial pH of 6.0.

The cells were centrifugated and collected after the fermentation, the dry cell weight in the fermentation broth was determined and reached 132 g/L, and gas chromatography showed the content of the DHA reached 30.5 g/L. The methods of treatment of the fermentation broth and the extraction and determination of the DHA were referenced to the methods disclosed in Chinese patent CN101638361A. The extracted DHA can be used as a nutrient supplement to provide the long-chain polyunsaturated fatty acid required by human and animals.

Example 4

The strain of *Schizochytrium* sp. S31 (ATCC No. 20888) was inoculated into a slant culture medium, cultured and activated at 28° C., cultured for 2 days. The formula of the slant culture medium was as follows: 30 g/L of glucose, 12 g/L of peptone, 3 g/L of yeast powder, 15 g/L of sea crystal and 20 g/L of agar powder, with the pH value of 6.5, sterilized at 121° C. for 30 min. When a culture period expired, the slant was added with 0.85% saline to wash the strain, a suspension of the train was obtained, and the cell concentration was controlled at $1.5 \times 10^6$/mL.

The obtained suspension of the strain was directly inoculated into a shake flask liquid culture medium (150 ml of liquid loading volume in a 500 ml flask) in an inoculation amount of 1%, with the shake flask shaking speed of 220 rpm, and cultured at 28° C. for 1 day, and the primary liquid seed was prepared. The shake flask liquid seed culture medium comprised 20 g/L of glucose, 22 g/L of sodium chloride, 0.2 g/L of potassium dihydrogen phosphate, 5 g/L of yeast powder, 12 g/L of magnesium sulfate heptahydrate, 0.3 g/L of sea salt and 0.8 g/L of glutamic acid, with a pH value of 6.5, sterilized at 121° C. for 30 min.

Under sterile conditions, the primary liquid seed was inoculated into a solid culture medium (the loading amount was 170 g/bottle subpackaged in 1000 ml of K bottle) in an inoculation amount of 15% in volume/weight fraction, the K bottle was shaked and uniformly mixed, cultured at 26° C. for 2 days, and the K bottle was shaked once every 8-12 h during the culture to uniformly mix so as to benefit the seed to make full use of the nutrient to grow. The secondary solid seed was prepared.

The secondary solid seed was added with sterile water in a ratio of 1:3 (W/V), oscillated to wash off the strain, and the cell concentration was controlled at $2.0 \times 10^6$/mL. An obtained suspension of the strain was inoculated into a 100 L fermentor in an inoculation amount of 10% for enlarging culture, and the volume after inoculation was 60 L. At the first 48 h of fermentation, the temperature was controlled at 25° C., the dissolved oxygen was kept at 30% by regulating the shaking speed and the ventilation, and from the $48^{th}$ hour to the end of the fermentation, the temperature was controlled at 20° C., the dissolved oxygen was maintained at about 10%, The sample was taken once every 8 h in the fermentation process to determine the residual sugar, the cell concentration, the dry cell weight and the content of DHA in fermentation broth, and the fermentation lasted for 4.5 days, when the cell begin to autolyze, the dry cell weight of cells and the yield of DHA were not increased, increased slowly or in a descending trend. The fermentation pH was controlled at 6.0 with 28% ammonia in weight percentage, and the concentration of glucose was controlled at 6 g/L via automatic feeding of 580 g/L glucose solution which was sterilized at 118° C. for 25 min in the whole fermentation process.

A preparation method of the solid culture medium was: the solid culture medium consisted of a solid component and a liquid component of nutrient solution component, wherein the solid component was millet with an amount of 350 g/L. The millet and component 1 of the liquid component of nutrient solution were uniformly mixed in a ratio of 10:4 (W/V), the cereal was steamed and boiled till no white cores existed at the centers of the cereals and the water content was 55%, and a raw material of the solid culture medium was obtained. The raw material of the solid culture medium and component 2 of the liquid component of nutrient solution were uniformly mixed in a ratio of 10:4 (W/V), the mixture was loaded with a thickness of 0.3 cm into a solid-state fermentation K bottle, subpackaged with a loading amount of 170 g/bottle in 1000 ml K bottle, sterilized at 121° C. for 30 min, and the solid culture medium was prepared.

Component 1 of the liquid nutrient solution comprised 3 g/L of glucose, 0.5 g/L of magnesium sulfate heptahydrate, 5.0 g/L of dipotassium hydrogen phosphate, 0.8 g/L of sea salt, 0.2 g/L of glycine, 1.6 g/L of threonine, 3.5 g/L of methionine, 3 g/L of malic acid, water was added to a required volume, and the pH value was adjusted to 6.0. The component 2 comprised 15 mg/L of $La^{3+}$, 4 mg/L of $Ce^{3+}$, 5 mg/L of $Sm^{3+}$, 10 mg/L of $Nd^{3+}$, 0.9 mg/L of $Mn^{2+}$, 0.1 mg/L of $Co^{2+}$, 0.4 mg/L of biotin, 0.2 mg/L of cerulenin, 2 mg/L of gibberellin GA, 1.0 mg/L of $VB_{12}$, 0.02 mg/L of folic acid and the balance of water.

The liquid fermentation culture medium comprised 40 g/L of glucose, 20 g/L of NaCl, 6 g/L of $MgSO_4.7H_2O$, 4 g/L of yeast powder, 1.0 g/L of $KH_2PO_4$, 0.5 g/L of $(NH_4)_2SO_4$, 0.8 g/L of $NaHCO_3$, 2.0 µg/L of $CoCl_2$, 0.5 µg/L of $MnSO_4$, 0.05 mg/L of $VB_1$ and 0.005 mg/L of $VB_{12}$, with an initial pH of 6.0.

The cells were centrifugated and collected after the fermentation, the dry cell weight in the fermentation broth was determined and reached 115 g/L, and gas chromatography showed the content of DHA reached 22.7 g/L. The methods of treatment of the fermentation broth and the extraction and determination of the DHA were referenced to the methods disclosed in Chinese patent CN101638361A. The extracted DHA can be used as a nutrient supplement to provide the long-chain polyunsaturated fatty acid required by human and animals.

Example 5

The strain of *Schizochytrium* sp. S8 (ATCC 20889) was inoculated into a slant culture medium, cultured and activated at 28° C., cultured for 2 days. The formula of the slant culture medium was as follows: 20 g/L of glucose, 12 g/L of peptone, 3 g/L of yeast powder, 20 g/L of sea crystal and 20 g/L of agar powder, with the pH value of 6.5, sterilized at 121° C. for 30 min. When a culture period expired, the slant was added with 0.85% to wash strain, a suspension of the strain was obtained, and the cell concentration was controlled at $2.5 \times 10^6$/mL.

The obtained suspension of the strain was directly inoculated into a shake flask liquid culture medium (350 ml liquid loading volume in 1 L flask) in an inoculation amount of 1%, with the shake flask shaking speed of 220 rpm, cultured at 28° C. for 1 day, and the primary liquid seed was prepared. The shake flask liquid seed culture medium comprised 25 g/L of glucose, 22 g/L of sodium chloride, 0.5 g/L of potassium dihydrogen phosphate, 5 g/L of yeast powder, 12 g/L of magnesium sulfate heptahydrate, 0.3 g/L of sea salt and 0.6 g/L of glutamic acid, with a pH value of 6.5, sterilized at 121° C. for 30 min.

Under sterile conditions, the primary liquid seed was inoculated into a solid culture medium (the loading amount was 2250 g/bottle subpackaged in 10 L of K bottle) in an inoculation amount of 12% in volume/weight fraction, the K bottle was shaked and uniformly mixed, cultured at 28° C. for 3 days, and the K bottle was shaked once every 8-12 h during the culture and uniformly mixed so as to benefit the seed to make full use of the nutrient to grow. The secondary solid seed was prepared.

The secondary solid seed was added with sterile water in a ratio of 1:4 (W/V), oscillated to wash off the strain with a controlled cell concentration of $2.0 \times 10^6$/mL. An obtained suspension of the strain was inoculated into a 1000 L fermentor in an inoculation amount of 18% for enlarging culture, and the volume after inoculation was 600 L. At the first 48 h of fermentation, the temperature was controlled at 28° C., the dissolved oxygen was kept at 30% by regulating the shaking speed and the ventilation, and from the $48^{th}$ hour to the end of the fermentation, the temperature was controlled at 20° C., the dissolved oxygen was maintained at about 10%. The sample was taken once every 8 h in the fermentation process to determine the residual sugar, the cell concentration, the dry cell weight and the content of DHA in fermentation broth, and the fermentation lasted for 5 days, when the cell begin to autolyze, the dry cell weight of cells and the yield of DHA were not increased, increased slowly or in a descending trend. The fermentation pH was controlled at 6.5 with 28% ammonia in weight percentage, and the concentration of glucose was controlled at 8 g/L via automatic feeding of 580 g/L of glucose solution which was sterilized at 118° C. for 25 min in the whole fermentation process.

A preparation method of the solid culture medium was: the solid culture medium consisted of a solid component and a liquid component of nutrient solution, wherein the solid component was rice with an amount of 300 g/L. The rice and component 1 of the liquid component of nutrient solution were uniformly mixed in a ratio of 8:5 (W/V), the cereal was steamed or boiled till no white cores existed at the centers of the cereals and the water content was 50%, and a raw material of the solid culture medium was obtained. The raw material of the solid culture medium and component 2 of the liquid component of nutrient solution were uniformly mixed in a ratio of 15:3 (W/V), and subpackaged with a thickness of 0.5 cm and a loading amount of 2250 g/bottle into 10 L of K bottle.

The liquid nutrient solution component 1 comprised 3 g/L of glucose, 0.5 g/L of magnesium sulfate heptahydrate, 5.0 g/L of dipotassium hydrogen phosphate, 0.8 g/L of sea salt, 0.2 g/L of glycine, 1.6 g/L of threonine, 3.5 g/L of methionine, 3 g/L of malic acid, water is added to a required volume, and the pH value was adjusted to 6.0. The component 2 comprises 15 mg/L of $La^{3+}$, 4 mg/L of $Ce^{3+}$, 5 mg/L of $Sm^{3+}$, 10 mg/L of $Nd^{3+}$, 1.2 mg/L of $Mn^{2+}$, 0.1 mg/L of $Co^{2+}$, 0.4 mg/L of biotin, 0.2 mg/L of cerulenin, 2 mg/L of gibberellin GA, 1.0 mg/L of $VB_{12}$, 0.02 mg/L of folic acid and the balance of water.

The liquid fermentation culture medium comprised 40 g/L of glucose, 20 g/L NaCl, 6 g/L of $MgSO_4.7H_2O$, 4 g/L of yeast powder, 1.0 g/L of $KH_2PO_4$, 0.5 g/L of $(NH_4)_2SO_4$, 0.8 g/L of $NaHCO_3$, 2.0 µg/L $CoCl_2$, 0.5 µg/L of $MnSO_4$, 0.05 mg/L of $VB_1$ and 0.005 mg/L of $VB_{12}$, with an initial pH of 6.5.

The cells were centrifugated and collected after the fermentation, the dry cell weight in the fermentation broth was determined and reached 138 g/L, and gas chromatography showed the content of the DHA reached 31.6 g/L. The methods of treatment of the fermentation broth and the extraction and determination of the DHA were referenced to the methods disclosed in Chinese patent CN101638361A. The extracted DHA can be used as a nutrient supplement to provide the long-chain polyunsaturated fatty acid required by human and animals.

Example 6

The strain of *Schizochytrium aggregatum* (ATCC 28209) was inoculated into a slant culture medium, cultured and activated at 25° C., cultured for 2 days. The formula of the slant culture medium was as follows: 20 g/L of glucose, 15 g/L of peptone, 3 g/L of yeast powder, 15 g/L of sea crystal and 20 g/L of agar powder, with pH value of 6.5, sterilized at 121° C. for 30 min. When a culture period expired, the slant was added with 0.85% saline to wash the strain, a suspension of the strain was obtained, and the cell concentration was controlled at $2.5 \times 10^6$/mL.

The obtained suspension of the strain was directly inoculated into a sterilized solid culture medium (the loading amount was 225 g/bottle and subpackaged into 1000 ml of K bottle) in an inoculation amount of 1% in volume/weight fraction, cultured at 28° C. for 1 day, and the K bottle was shaken once every 8-12 h during the culture to uniformly mix so as to benefit the seed to make full use of the nutrient to grow. The primary solid seed was prepared.

Under sterile conditions, the primary solid seed (the primary solid seed used for inoculation was added with 0.85% saline in a ratio of 1:1 (W/V) to wash the strain, prepared as a suspension of the strain with a controlled cell concentration of $1.5 \times 10^6$/mL) and was inoculated into a solid culture medium (the loading amount was 2250 g/bottle and subpackaged into 10 L of K bottle) in an inoculation amount of 20% in volume/weight fraction, the K bottle was shaken for uniformly mixing, cultured at 25° C. for 3 days, and the K bottle was shaken once every 8-12 h during the culture and uniformly mixed so as to benefit the seed to make full use of the nutrient to grow. The secondary solid seed was prepared.

The secondary solid seed was added with sterile water in a ratio of 1:4 (W/V), oscillated to wash off the strain, and the cell concentration was controlled at $2.0 \times 10^6$/mL. An obtained suspension was inoculated into a 1000 L fermentor in an inoculation amount of 12% for enlarging culture, and the volume after inoculation was 600 L. At the first 48 h of the fermentation, the temperature was controlled at 28° C., the dissolved oxygen was kept at 40% by regulating the shaking speed and the ventilation, and from the $48^{th}$ hour to the end of the fermentation, the temperature was controlled at 18° C., the dissolved oxygen was controlled at about 10%. The sample was taken once every 8 h in the fermentation process to determine the residual sugar, the cell concentration, the dry cell weight and the content of DHA in fermentation broth, and the fermentation lasted for 5 days, when the cell begin to autolyze, the dry cell weight of cells and the yield of DHA were not increased, increased slowly or in a descending trend. The fermentation pH was controlled at 6.5 with 28% ammonia in weight percentage, and the concentration of glucose was controlled at 8 g/L via automatic feeding of 580 g/L of glucose solution which was sterilized at 118° C. for 25 min in the whole fermentation process.

A preparation method of the solid culture medium was: the solid culture medium consisted of a solid component and a liquid component of nutrient solution, wherein the solid component was barley with an amount of 375 g/L. The barley and component 1 of the liquid component nutrient solution were uniformly mixed in a ratio of 8:3 (W/V), the cereal was steamed or boiled till no white cores existed at the centers of the cereals and the water content was 55%, and a raw material of the solid culture medium was obtained. The raw material of the solid culture medium and component 2 of the liquid component of nutrient solution were uniformly mixed in a ratio of 10:3 (W/V), subpackaged with a thickness of 0.5 cm and a loading amount of 2250 g/bottle into 10 L of K bottle or subpackaged with a loading amount of 225 g/bottle into 1 L of K bottle.

Component 1 of the liquid nutrient solution comprised 5 g/L of glucose, 0.2 g/L of magnesium sulfate heptahydrate, 3.0 g/L of dipotassium hydrogen phosphate, 0.6 g/L of sea salt, 0.6 g/L of glycine, 1.5 g/L of threonine, 2 g/L methionine, 4 mg/L of malic acid, water was added to a required volume, and the pH value was adjusted to 6.5. The component 2 comprised 15 mg/L of $La^{3+}$, 2 mg/L of $Ce^{3+}$, 3 mg/L of $Sm^{3+}$, 8 mg/L of $Nd^{3+}$, 1.2 mg/L of $Mn^{2+}$, 0.08 mg/L of $Co^{2+}$, 0.2 mg/L of biotin, 0.1 mg/L of cerulenin, 5 mg/L of gibberellin GA, 1.0 mg/L of $VB_{12}$, 0.03 mg/L of folic acid and the balance of water.

The liquid fermentation culture medium comprised 30 g/L of glucose, 20 g/L of NaCl, 5 g/L of $MgSO_4 \cdot 7H_2O$, 3 g/L of yeast powder, 1.0 g/L of $KH_2PO_4$, 0.4 g/L of $(NH_4)_2SO_4$, 1.2 g/L of $NaHCO_3$, 2.0 µg/L of $CoCl_2$, 0.7 µg/L of $MnSO_4$, 0.06 mg/L of $VB_1$ and 0.005 mg/L of $VB_{12}$, with an initial pH of 6.5.

The cells were centrifugated and collected after the fermentation, the dry cell weight in the fermentation broth was determined and reached 142 g/L, and gas chromatography showed the content of DHA reached 32.3 g/L. The methods of treatment of the fermentation liquor and the extraction and determination of DHA were referenced to the methods disclosed in Chinese patent CN101638361 A. The extracted DHA can be used as a nutrient supplement to provide the long-chain polyunsaturated fatty acid required by human and animals.

Although the embodiments of the invention are described in detail, a person skilled in the art would understand that various modification and substitutions may be made to these details on the basis of all the teachings disclosed. These changes fall into the protection scope of the invention. The scope of the invention is defined by the attached claims and an equivalent thereof.

What is claimed is:

1. A method for producing DHA through solid culture and liquid fermentation of *Schizochytrium*, which comprises the following steps:
   (1) activating a strain, wherein a *Schizochytrium* strain is inoculated into a culture medium, cultured and activated to prepare a suspension of the strain;
   (2) preparing a primary seed, wherein the suspension of the strain obtained in step (1) is inoculated into a solid culture medium and cultured to obtain a primary solid seed; or wherein the suspension of the strain obtained in step (1) is inoculated into a liquid seed culture medium and cultured to obtain a primary liquid seed;
   (3) preparing a secondary solid seed, wherein the primary solid seed is prepared as a solution of the primary solid seed, which is inoculated into a solid culture medium and cultured; or wherein the primary liquid seed solution is inoculated into a solid culture medium and cultured; whereby a secondary solid seed is obtained;
   (4) enlarging culture of the secondary solid seed in a fermentor, wherein the secondary solid seed is prepared as a solution of the secondary solid seed, which is inoculated into a liquid culture medium in a fermentor for enlarging culture; and
   (5) collecting cells after fermentation and extraction of DHA;
   wherein the solid culture medium in step (2) or step (3) comprises a solid component and a liquid component of nutrient solution, wherein the solid component is cereal with an amount of 250-400 g/L, wherein the cereal is selected from the group consisting of rice, wheat and corn, wherein the rice is selected from the group consisting of rice, millet and unpolished rice, and wherein the wheat is selected from the group consisting of barley, wheat and oat;

wherein the liquid component of nutrient solution comprises component 1 and component 2, wherein the component 1 comprises 2-5 g/L of glucose, 0.2-0.6 g/L of magnesium sulfate heptahydrate, 1.0-5.0 g/L of dipotassium hydrogen phosphate, 0.1-0.8 g/L of sea salt, 0.2-0.6 g/L of glycine, 1.5-1.8 g/L of threonine, 2-3.5 g/L of methionine, 3-6 g/L of malic acid, water is added to a metered volume, and the pH value is adjusted to 6-7; and wherein the component 2 comprises 10-15 mg/L of $La^{3+}$, 1-4 mg/L of $Ce^{3+}$, 2-6 mg/L of $Sm^{3+}$, 8-12 mg/L of $Nd^{3+}$, 0.6-1.2 mg/L of $Mn^{2+}$, 0.05-0.1 mg/L of $Co^{2+}$, 0.2-0.6 mg/L of biotin, 0.1-0.3 mg/L of cerulenin, 2-5 mg/L of gibberellin GA, 0.5-1.0 mg/L of $VB_{12}$, 0.01-0.05 mg/L of folic acid and the balance of water;

wherein the preparation method of the solid culture medium comprises: mixing uniformly the solid component and component 1 of the liquid component of nutrient solution, steaming or boiling the cereal till no white cores exist at the centers of the cereal and the water content is 50%-65%, whereby a raw material of the solid culture medium is obtained; mixing uniformly the raw material of the solid culture medium and component 2 of the liquid component of nutrient solution, and loading the resulting mixture with a thickness of 0.2-1.0 cm into a solid fermentation bottle, and sterilizing, whereby the solid culture medium is obtained.

2. The method of claim 1, wherein the *Schizochytrium* is *Schizochytrium* sp. selected from the group consisting of *Schizochytrium* sp. KDW-12, *Schizochytrium* sp. S31, *Schizochytrium aggregatum* and *Schizochytrium* sp. S8.

3. The method of claim 1, wherein step (1) is characterized by one or more of the following items:
   a. the culture temperature is 25-28° C., and the culture is performed till the cell concentration and cell morphology are good; and
   b. the cell concentration of the suspension of the strain is $1.0-2.5\times10^6$/mL.

4. The method of claim 1, wherein step (2) is characterized by one or more of the following items:
   a. the inoculation amount is 0.5-2%;
   b. the culture temperature is 25-28° C., and the culture is performed till the cell concentration and cell morphology are good; and
   c. the liquid culture is subject to shaking at a speed of 180-220 rpm.

5. The method of claim 1, wherein step (3) is characterized by one or more of the following items:
   a. the cell concentration of the solution of the primary solid seed is $1.0-2.5\times10^6$/mL;
   b. the solution of the primary solid seed is inoculated into the solid culture medium in an inoculation amount of 10%-20% in volume/weight fraction;
   c. the primary liquid seed is inoculated into the solid material culture medium in an inoculation amount of 8%-15% in volume/weight fraction; and
   d. the culture temperature is 25-28° C., and the culture is performed till the cell concentration and cell morphology are good.

6. The method of claim 1, wherein step (4) is characterized by one or more of the following items:
   a. the solution of the secondary solid seed is inoculated into the fermentor for enlarging culture in an inoculation amount of 10%-20% in volume fraction;
   b. at the first 48 h of the fermentation, the temperature is controlled at 25-28° C. and the dissolved oxygen is kept at 30%-50% by regulating the shaking speed;
   c. the temperature is controlled at 18-22° C. from the 48th hour to the end of the fermentation;
   d. the fermentation is terminated when the cell begin to autolyze, the dry cell weight and the yield of DHA are not increased, increased slowly or in a descending trend;
   e. the pH of fermentation broth is controlled at 6.0-6.5 with ammonia during the fermentation; and
   f. the concentration of glucose is controlled at 4-8 g/L via automatic feeding of glucose solution during the fermentation.

7. The method of claim 1, wherein the culture medium is a slant culture medium in step (1) containing 20-30 g/L of glucose, 10-15 g/L of peptone, 3-5 g/L of yeast powder, 15-20 g/L of sea crystal and 15-25 g/L of agar powder, with a pH value of 6.0-7.0.

8. The method of claim 1, wherein the liquid seed culture medium in step (2) contains 20-25 g/L of glucose, 20-25 g/L of sodium chloride, 0.2-0.5 g/L of potassium dihydrogen phosphate, 3-5 g/L of yeast powder, 8-12 g/L of magnesium sulfate heptahydrate, 0.1-0.8 g/L of sea salt and 0.2-0.6 g/L of glutamic acid, with a pH value of 6.0-7.0.

9. The method of claim 1, wherein the liquid culture medium in the fermentor in step (4) contains 30-60 g/L of glucose, 15-20 g/L of NaCl, 4-8 g/L of $MgSO_4 \cdot 7H_2O$, 3-8 g/L of yeast powder, 0.5-1.0 g/L of $KH_2PO_4$, 0.2-0.5 g/L of $(NH_4)_2SO_4$, 0.8-1.2 g/L of $NaHCO_3$, 1.0-2.0 µg/L of $CoCl_2$, 0.5-1.0 µg/L of $MnSO_4$, 0.05-0.1 mg/L of $VB_1$ and 0.001-0.01 mg/L of $VB_{12}$, with an initial pH value of 6.0-7.0.

* * * * *